United States Patent [19]

Kawamatsu et al.

[11] Patent Number: 4,486,594
[45] Date of Patent: Dec. 4, 1984

[54] THIAZOLIDINE DERIVATIVES AND PRODUCTION THEREOF

[75] Inventors: Yutaka Kawamatsu, Kyoto; Takeshi Fujita, Takarazuka; Yujiro Yamamoto, Suita, all of Japan

[73] Assignees: Takeda Chemical Industries, Ltd.; Senju Pharmaceutical Co., Ltd., both of Osaka, Japan

[21] Appl. No.: 484,549

[22] Filed: Apr. 13, 1983

[30] Foreign Application Priority Data

Apr. 13, 1982 [JP] Japan .................. 57-62223

[51] Int. Cl.³ .................. C07D 277/34; A61K 31/425
[52] U.S. Cl. .................................... 548/183; 424/270
[58] Field of Search ........................................ 548/183

[56] References Cited

U.S. PATENT DOCUMENTS 4,376,777 3/1983 Kawamatsu et al. ............... 424/270
4,387,101 6/1983 Kawamatsu et al. ............... 424/270

Primary Examiner—Robert Gerstl
Attorney, Agent, or Firm—Wenderoth, Lind & Ponack

[57] ABSTRACT

A new thiazolidine derivative of the formula:

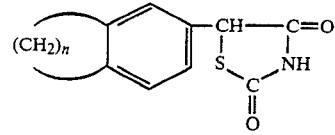

wherein n stands for an integer of 3 to 6 and salts thereof show strong aldose reductase inhibition and are useful for prophylaxis or therapy of diabetic cataracts and diabetic neuropathy in mammals.

4 Claims, No Drawings

THIAZOLIDINE DERIVATIVES AND PRODUCTION THEREOF

This invention relates to novel thiazolidine derivatives useful as prophylactic and therapeutic agents against diabetic complications such as diabetic cataracts or diabetic neuropathy, and the production thereof.

More specifically, this invention relates to thiazolidine derivatives of the formula:

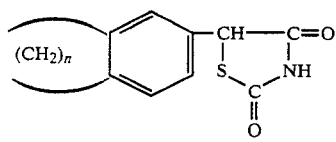

wherein n denotes an integer of 3 to 6, preferably 3,4 or 5, and a method for production of the compound (I) which comprises hydrolyzing a compound of the formula:

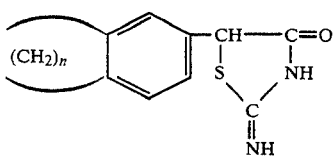

wherein n has the same meaning as above.

The compounds (I) are acid substances and are capable of forming basic salts, e.g. sodium salts, potassium salts, calcium salts or ammonium salts.

Thiazolidine derivatives (I) or salts thereof of this invention are strong aldose reductase inhibitors and remarkably inhibit the accumulation of sorbitol in the lens or nerve fiber in diabetic rats induced by streptozotosin, and they are used for prophylaxis or therapy of diabetic cataracts, diabetic neuropathy, etc. in mammals, for instance, mouse, rat, dog and human being.

Further, the compounds (I) or their salts are less toxic, the oral $LD_{50}$ for, for example, 5-(5,6,7,8-tetrahydro-2-naphthyl)thiazolidine-2,4-dione in mice being no less than 100 mg., and they can be safely administered for a long period of time. When the compounds (I) or their salts are administered for ophthalmic use, they do not cause irritation and can inhibit accumulation of sorbitol in the lens and thus can serve in ophthalmic use in treating cataracts. The compounds (I) or their salts may for example be administered orally in such dosage forms as tablets, capsules, powders and granules, parenterally in the form of injections and pellets, or locally as ophthalmic solutions. The dosage is usually 50 mg to 1000 mg daily per adult human, when given orally, in 1 to 4 divided doses a day. For ophthalmic use, 0.001 to 1% ophthalmic solution is desirably administered to the eye at the frequency of 3 to 5 times daily, one to a few drops a time.

The thiazolidine derivatives (I) of this invention can be produced by the following manner:

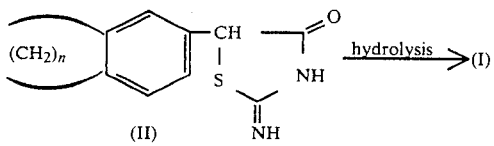

In the formulae, n has the same meaning as above.

The hydrolysis is conducted preferably in the presence of an acid in a suitable solvent.

As the suitable solvents, there may for example be mentioned alkanols, e.g. methanol, ethanol, propanol or methoxyethanol, ethers, e.g. tetrahydrofuran or dioxane, acetone, dimethylformamide, dimethyl sulfoxide or sulfolane. As the acid, there may preferably be mentioned mineral acids, e.g. sulfuric acid or hydrochloric acid. The amount of the acid to be added is usually within the range of from 1 mole to 50 moles, preferably from 2 to 30 moles relative to the compound (II) employed. The amount of water to be added is usually in large excess. The hydrolysis reaction is preferably conducted at an elevated temperature, e.g. 30° to 150° C.

The thus-obtained object compound (I) can be isolated and purified by a conventional means such as concentration, solvent-extraction, recrystallization, chromatography, or the like. The compound (I) which is an acid compound can be converted to a salt with, for example, alkali metal, alkaline earth metals or organic bases such as sodium, potassium, calcium, amines, and the like.

The compound (II) can be synthesized, for example, by the following manner.

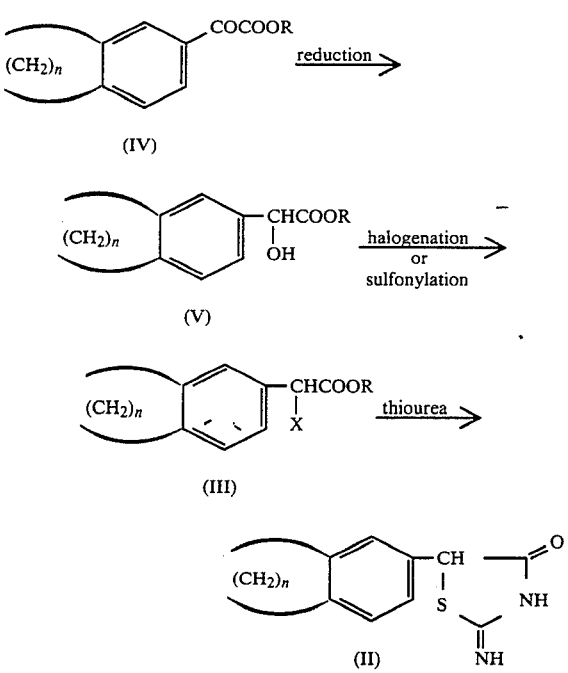

In the formulae, R stands for hydrogen, alkyl or aralkyl, X stands for a group to be eliminated, and n has the same meaning as above.

As the alkyl group represented by R, preferable are those having 1-4 carbon atoms, e.g. methyl, ethyl, propyl, isopropyl, n-butyl, isobutyl, sec.-butyl or t-butyl. As the aralkyl group represented by R, there may preferably be mentioned a phenyl lower alkyl, e.g. benzyl or phenylethyl.

The group to be eliminated, represented by X, is exemplified by halogen, e.g. chlorine or bromine, or a sulfonyloxy group, e.g. mesyloxy, tosyloxy or benzenesulfonyloxy. n denotes an integer of 3–6, and especially preferable are 3, 4 and 5.

Glyoxylic acid derivatives of the formula (IV) and their reduction products (V) can be synthesized by the method described in Austrian Patent No. 344153 (1978) (C.A. 89, P179741e (1978)) or a method analogous thereto.

The compound (III) can be obtained by halogenation or sulfonylation of the compound (V).

The halogenation is carried out by reacting a halogenating agent such as phosphorus tribromide, thionyl chloride and phosphorus oxychloride with the compound (V) in the absence or presence of a suitable solvent such as dichloromethane and chloroform. The reaction is preferably conducted at an elevated temperature, for example, 20° to 100° C.

Sulfonylation of a compound (V) can be conducted by reacting the compound (V) with sulfonylating agent, e.g. mesyl chloride, tosyl chloride or benzenesulfonyl chloride at 0°–60° C. in a suitable solvent, e.g. benzene, ethyl acetate, dichloromethane or chloroform in the presence of a base, e.g. pyridine or triethylamine.

The compound (III) thus produced is allowed to react with thiourea to synthesize a compound (II), which is then subjected to hydrolysis to obtain the object compound (I). The reaction between a compound (III) and thiourea is usually conducted in a solvent. The solvents are exemplified by alkanols, e.g. methanol, ethanol, propanol or methoxyethanol, ethers, e.g. tetrahydrofuran or dioxane, acetone, dimethylformamide, dimethylsulfoxide or sulfolane. The amount of thiourea to be used is preferably 1–2 moles, relative to 1 mole of the compound (III) employed. The reaction temperature usually ranges from 50° C. to 150° C., preferably 60° to 130° C.

The thus-produced compound (II) can be isolated in an optional purity by means of a conventional separation and purification method, for example, concentration, solvent-extraction, recrystallization or chromatography, or can be coverted to the compound (I) by subjecting the reaction mixture to the subsequent hydrolysis directly without isolating the compound (II).

The following reference examples, working examples and experimental data are given to further illustrate this invention.

REFERENCE EXAMPLE 1

Anhydrous aluminum chloride (9.1 g) was suspended in dichloromethane (80 ml). To the suspension was added dropwise, while stirring under cooling, ethoxalyl chloride (9.2 g), followed by addition thereof of 6,7,8,9-tetrahydro-5H-benzocycloheptadiene (9.0 g) dissolved in dichloromethane (10 ml). The mixture was stirred for 30 minutes under ice-cooling, and poured into ice-water. Then the resulting organic layer was separated, washed with water and dried over anhydrous magnesium sulfate, then the solvent was evaporated off. The residue was subjected to distillation under reduced pressure to leave 10.7 g(70.4%) of ethyl 6,7,8,9-tetrahydro-5H-benzocycloheptadien-2-yl-glyoxylate as an oily substance, b.p. 153°–155° C./0.2 mmHg.

IR (Neat); 1735, 1685 cm$^{-1}$.

NMR (CDCl$_3$)δ: 1.39(3H,t,J=7), 1.75(6H,broad s), 2.65–2.95(4H,m), 4.40(2H,q,J=7), 7.10(1H,d,J=9), 7.6(2H,m).

REFERENCE EXAMPLE 2

By the same procedure as that in Reference Example 1, except for employing tetralin as the starting material, ethyl 5,6,7,8-tetrahydro-2-naphthylglyoxylate, b.p. 148°–153° C./0.3 mmHg. was prepared. The yield was 70.5%.

IR (Neat): 1735, 1680 cm$^{-1}$.

NMR(CDCl$_3$)δ: 1.38(2H,t,J=7), 1.6–2.0(4H,m), 2.75(4H,broad s), 4.40(2H,q,J=7), 7.10(1H,d,J=9), 7.6(2H,m).

REFERENCE EXAMPLE 3

By the same procedure as that in Reference Example 1, except for employing indane as the starting material, ethyl 5-indanylglyoxylate was prepared. The yield was 74.8%.

IR (Neat): 1735, 1680 cm$^{-1}$.

NMR (CDCl$_3$)δ: 1.40(3H,t,J=7), 1.8–2.4(2H,m), 2.93(4H,t,J=7), 4.40(2H,q,J=7), 7.18(1H,d,J=9), 7.5–7.7(2H,m).

REFERENCE EXAMPLE 4

To ethyl 6,7,8,9-tetrahydro-5H-cycloheptadien-2-yl glyoxylate (10.3 g) dissolved in ethanol (50 ml) was added sodium borohydride (0.95 g) under ice-cooling, and the mixture was then stirred for 30 minutes. To the mixture was added dropwise acetic acid (4 ml), and the whole mixture was poured into water, followed by extraction with ethyl ether. The ether layer was washed with water, saturated aqueous solution of sodium bicarbonate and water, in that order, then dried over anhydrous magnesium sulfate. Removal of ethylether by evaporation left ethyl 2-hydroxy-2-(6,7,8,9-tetrahydro-5H-benzocycloheptadien-2-yl)acetate as an oily product. The yield was 10.48 (100%).

IR (Neat): 3470, 1730 cm$^{-1}$.

NMR (CDCl$_3$):δ 1.20(3H,t,J=7), 1.7(6H,broad s), 2.6–2.9(4H,m), 3.57(1H,d,J=6, D$_2$O disappear), 4.18(2H,q,J=7), 5.00(1H,d,J=6, D$_2$O changed to s), 7.00(3H, broad s).

REFERENCE EXAMPLE 5

Ethyl 5,6,7,8-tetrahydro-2-naphthylglyoxylate was subjected to reduction in the same manner as in Reference Example 4 to prepare ethyl 2-hydroxy-2-(5,6,7,8-tetrahydro-2-naphthyl)acetate as an oily product. The yield was 92.8%.

IR (Neat): 3480, 1735 cm$^{-1}$.

NMR (CDCl$_3$)δ: 1.18(3H,t,J=7), 1.6–2.0(4H,m), 2.75(4H,broad s), 3.60(1H,broad s, D$_2$O disappear), 4.18(2H,q,J=7), 5.03(1H,s), 6.8–7.2(3H,m).

REFERENCE EXAMPLE 6

Ethyl 5-indanylglyoxylate was subjected to reduction in the same manner as in Reference Example 4 to prepare ethyl 2-hydroxy-2-(5-indanyl)acetate as an oily product. The yield was 92.9%.

IR (Neat): 3480, 1735 cm$^{-1}$.

NMR(CDCl$_3$)δ: 1.17(3H,t,J=7), 1.8–2.4(2H,m), 2.83(4H,t,J=7), 3.80(1H,d,J=6, D$_2$O disappear), 4.13(2H,q,J=7), 5.05(1H,d,J=6, D$_2$O change to s), 7.1–7.4(3H,m).

REFERENCE EXAMPLE 7

A mixture of ethyl 2-hydroxy-2-(6,7,8,9-tetrahydro-(5H-benzocycloheptadien-2-yl)acetate (10.0 g) and thionyl chloride (20 ml) was subjected to reflux for one hour. Excess thionyl chloride was evaporated off under reduced pressure. The remaining oily substance was further subjected to distillation under reduced pressure to leave ethyl 2-chloro-2-(6,7,8,9-tetrahydro-5H-benzocycloheptadien-2-yl) acetate as an oily product, b.p. 145°–148° C./0.2 mmHg. The yield was 9.5 g (88.8%).

IR (Neat): 1750 cm$^{-1}$.

NMR(CDCl$_3$)$\delta$: 1.23(3H,t,J=7), 1.7(6H,broad s), 2.65–2.95(4H,m), 4.17(2H,q,J=7), 5.22(1H,s), 7.0–7.3(3H,m).

REFERENCE EXAMPLE 8

Ethyl 2-hydroxy-2-(5,6,7,8-tetrahydro-2-naphthyl)acetate was processed in the same manner as in Reference Example 7 to prepare ethyl 2-chloro-2-(5,6,7,8-tetrahydro-2-naphthyl)acetate as an oily product, b.p. 139°–142° C./0.3 mmHg. The yield was 94.5%.

IR (Neat): 1750 cm$^{-1}$.

NMR(CDCl$_3$)$\delta$: 1.23(3H,t,J=7), 1.6–2.0(4H,m), 2.75(4H,broad s), 4.18(2H,q,J=7), 5.25(1H,s), 6.9–7.4(3H,m).

REFERENCE EXAMPLE 9

Ethyl 2-hydroxy-2-(5-indanyl)acetate was processed in a manner similar to that of Reference Example 7 to give ethyl 2-chloro-2-(5-indanyl)acetate as an oily substance, b.p. 128°–132° C./0.3 mmHg. The yield was 92.1%.

IR (Neat): 1750 cm$^{-1}$.

NMR(CDCl$_3$)$\delta$: 1.20(3H,t,J=7), 1.8–2.2(2H,m), 2.83(4H,t,J=7), 4.15(2H,q,J=7), 5.25(1H,s), 7.0–7.3(3H,m).

EXAMPLE 1

Thiourea (3.0 g) was added to ethyl 2-chloro-2-(6,7,8,9-tetrahydro-5H-benzocycloheptadien-2-yl)acetate (9.0 g) dissolved in ethanol (100 ml). The mixture was stirred for two hours under reflux, and 2N-HCl (50 ml) was added thereto. The mixture was refluxed for a further 12 hours, cooled and poured into water. The resulting crystals were collected by filtration to yield 8.0 g (90.9%) of 5-(6,7,8,9-tetrahydro-5H-benzocycloheptadien-2-yl)thiazolidine-2,4-dione. Recrystallization from 80% aqueous ethanol yielded colorless prisms, m.p. 137°–138° C.

Elemental Analysis for C$_{14}$H$_{15}$NO$_2$S: Calcd.: C 64.59; H 5.42; N 5.38. Found: C 64.33; H 5.72; N 5.15.

EXAMPLE 2

Ethyl 2-chloro-2-(5,6,7,8-tetrahydro-2-naphthyl)acetate was allowed to react with thiourea in a manner similar to that in Example 1, then the reaction mixture was subjected to hydrolysis to yield crystals of 5-(5,6,7,8-tetrahydro-2-naphthyl)thiazolidine-2,4-dione. The yield was 92.3%. Recrystallization from 75% aqueous ethanol gave colorless plates, m.p. 157°–158° C.

Elemental Analysis for C$_{13}$H$_{13}$NO$_2$S: Calcd.: C 63.14; H 5.30; N 5.66. Found: C 63.35; H 5.15; N 5.66.

EXAMPLE 3

2.47 g of 5-(5,6,7,8-tetrahydro-2-naphthyl)thiazolidine-2,4-dione was dissolved in 100 ml of ethyl acetate. To the solution was added 2 ml of 28% methanol solution of sodium methylate, whereupon fine crystals precipitated. Ethyl acetate was evaporated off. To the residue was added ethyl ether, and then the resulting fine crystals were collected by filtration. Recrystallization from methanol yielded 2.01 g (74.7%) of 5-(5,6,7,8-tetrahydro-2-naphthyl)thiazolidine-2,4-dione as prisms. The melting point was higher than 300° C.

IR (Nujol)cm$^{-1}$: 1670, 1565, 1320, 1250.

NMR (d$_6$-DMSO)$\delta$: 1.70(4H,bs), 2.32(4H,bs), 4.97(1H,s), 6.93(3H,s).

Elemental Analysis for C$_{13}$H$_{12}$NO$_2$S.Na: Calcd.: C 57.98; H 4.49; N 5.20. Found: C 57.91; H 4.28; N 5.49.

EXAMPLE 4

Ethyl 2-chloro-2-(5-indanyl)acetate was allowed to react with thiourea in a manner similar to Example 1. The reaction mixture was then subjected to hydrolysis to yield crystals of 5-(5-indanyl)thiazolidine-2,4-dione. The yield was 83.3%. Recrystallization from ethanol afforded colorless plates, m.p. 124°–125° C.

Elemental Analysis for C$_{12}$H$_{11}$NO$_2$S: Calcd.: C 61.78; H 4.75; N 6.00. Found: C 61.67; H 4.67; N 5.89.

EXPERIMENT (1) Test compounds

The following Experiments were carried out on the compounds of the two groups, one group consisting of the present compounds and the other group consisting of the known compounds which are thought to be the closest in chemical structure to the present compounds and are disclosed in European Patent Publication No. 33617.

(2) Aldose Reductase Inhibitory Action:

Aldose reductase inhibitory action was assayed in accordance with the method disclosed by S. Haymen et al. in Journal of Biological Chemistry, Vol. 240, p. 877 (1965) and that disclosed by Jin H. Kinoshita et al. in Metabolism, Vol. 28, Nr. 4, Suppl. 1, 462 (1979). The enzyme used in the assay was a partially purified aldose reductase preparation from human placenta. The results for the respective compounds were expressed as % inhibition at the concentration of 10$^{-6}$ mole and are shown in Table 1.

(3) Inhibition of Sorbitol Accumulation in the tissue of rats

Sprague-Dawley rats (male, 5–7 week old, five rats/group) were fasted for 18 hours. The rats were made diabetic by an intravenous injection of 70 mg/kg of streptozotocin (Produced by Cal Biochem) at the site of the tail under ether anesthesia. After the administration of streptozotocin, these rats were administered orally with 25 mg/kg of the test compounds (5% suspension of gum-arabica) for two days twice a day (at 9.00 a.m. and at 4.00 p.m.). During this period, these rats were allowed free access to CE-2 feedstuff (Produced by Clea Japan) and water while determining blood-sugar level of each animal. On the morning of the third day, these rats were decapitated and bled, then the lens and sciatic nerve were quickly excised. The respective contents of sorbitol in the lens and sciatic nerve were determined by the enzymatic assay method described by R. S. Clements et al., in Science, 166, p. 1007 (1969) applied to the extracts of these organs obtained by the method described by M. J. Peterson et al., in Metabolism, 28, 456 (1979).

The results are shown in the Table below as % inhibition relative to the control. Incidentally, no significant difference in blood-sugar level was observed between the group of test animals to which the test compounds were administered and the control group of the test animals to which no test compounds were administered.

TABLE

| Test Compounds | | | Aldose Reductase Inhibition % $10^{-6}$M | Inhibition of Sorbitol Accumulation (%) | |
|---|---|---|---|---|---|
| | | | | Lens | Sciatic Nerve |
| Present Compounds | | | | | |
| Compound (I) | n | 3 | 30.0 | 62 | 66 |
| | | 4 | 36.0 | 73 | 79 |
| | | 5 | 34.0 | 65 | 83 |
| Comparative Compounds | | | | | |
| 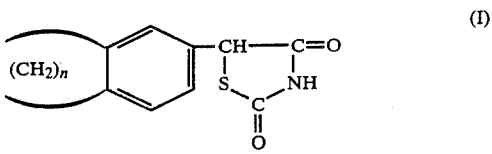 | | | 35.8 | 18 | 5 |

TABLE-continued

| Test Compounds | Aldose Reductase Inhibition % $10^{-6}$M | Inhibition of Sorbitol Accumulation (%) | |
|---|---|---|---|
| | | Lens | Sciatic Nerve |
| (structure: 3,4-dimethoxyphenyl) | 57.1 | 62 | −2 |

What is claimed is:

1. A compound of the formula:

(I)

wherein n stands for an integer of 3 to 6, or a pharmaceutically acceptable salt thereof.

2. A compound as claimed in claim 1, wherein n is 3.
3. A compound as claimed in claim 1, wherein n is 4.
4. A compound as claimed in claim 1, wherein n is 5.

* * * * *